(12) United States Patent
Zavrel et al.

(10) Patent No.: US 10,519,477 B2
(45) Date of Patent: Dec. 31, 2019

(54) SELF-SUFFICIENT PROCESS FOR THE PRODUCTION OF BIOMASS HYDROLYSATE WITH REDUCED SALT CONTENT

(71) Applicant: Clariant International Ltd., Muttenz (CH)

(72) Inventors: Michael Zavrel, Olching (DE); Danielle Dennewald, München (DE); Philip Hoffmann, München (DE); Marcus Verhuelsdonk, Germering (DE)

(73) Assignee: Clariant International Ltd., Muttenz (CH)

( * ) Notice: Subject to any disclaimer, the term of this patent is extended or adjusted under 35 U.S.C. 154(b) by 106 days.

(21) Appl. No.: 15/758,727

(22) PCT Filed: Aug. 19, 2016

(86) PCT No.: PCT/EP2016/069739
§ 371 (c)(1),
(2) Date: Mar. 9, 2018

(87) PCT Pub. No.: WO2017/042018
PCT Pub. Date: Mar. 16, 2017

(65) Prior Publication Data
US 2018/0274000 A1    Sep. 27, 2018

(30) Foreign Application Priority Data

Sep. 11, 2015 (EP) .................................... 15184895

(51) Int. Cl.
*C12P 19/20* (2006.01)
*C12P 19/14* (2006.01)
(Continued)

(52) U.S. Cl.
CPC .............. *C12P 19/20* (2013.01); *C12P 19/02* (2013.01); *C12P 19/14* (2013.01); *C13K 1/02* (2013.01);
(Continued)

(58) Field of Classification Search
CPC ......... C04B 18/08; C04B 28/02; C04B 14/26; C04B 14/28; C04B 28/14; C04B 18/162; C04B 18/141; C04B 22/106; C04B 14/04; C04B 20/023; C04B 2103/0088; C04B 22/10; C04B 28/26; C04B 14/042; C04B 14/106; C04B 18/241; C04B 20/0048; C04B 2103/10; C04B 2103/22; C04B 2103/30; C04B 2103/67; C04B 2111/00017; C04B 2290/20; C04B 24/2623; C04B 38/0074; C04B 38/10; C04B 40/0231; C04B 7/02; C04B 7/436; C04B 16/04; C04B 2103/0086; C04B 2111/0062; C04B 2111/00629; C04B 28/006; C04B 28/04; C04B 28/18; C04B 7/367; C12P 19/02; C12P 19/14; C12P 2201/00; C12P 2203/00; C12P 13/04; C12P 19/12; C12P 19/20; C12P 5/002; C12P 5/02; C12P 5/026; C12P 7/10; C12P 7/26; C12P 7/28; C12P 7/40; B01D 2257/504; B01D 53/62; B01D 2251/402; B01D 2251/404; B01D 2257/302; B01D 2257/404; B01D 11/0207; B01D 11/0211; B01D 11/0257; B01D 15/08; B01D 2251/60; B01D 2251/602; B01D 2257/60; B01D 2257/602; B01D 3/06; B01D 53/1425; B01D 53/1475; B01D 53/1493; B01D 53/48; B01D 53/505; B01D 53/77; C01F 5/24; C01F 11/181; C01F 11/18; C01F 11/182; C01P 2002/72; C01P 2002/82; C01P 2002/88; C01P 2004/03; C01P 2004/61; C01P 2006/12; C01P 2006/80; C01P 2004/10; C01P 2004/60; C07K 14/37; C07K 14/38; C07K 14/385; C07K 14/405; C07K 1/12; C07K 1/22; C07K 1/24; C07K 1/36; C07K 4/08; C12N 9/2437; C12N 9/2445; C12N 9/96; C12N 13/00; C12Y 302/01004; C12Y 302/01021; C13K 1/02; D21C 1/02; D21C 1/04; Y02C 10/04; Y02C 10/06; Y02E 50/16; Y02E 20/16; Y02E 20/18; Y02P 20/129; Y02P 40/123; Y02P 40/18; Y02P 10/143; Y02P 20/152; Y02P 30/446; Y02P 40/165; Y02W 10/33; Y02W 10/37; Y02W 30/84; Y02W 30/92; Y02W 30/94; Y02W 30/95; Y02W 30/97; B01J 19/0093; B01J 19/24; B01J 2219/00864; B01J 2219/00867; B01J 2219/00871; B01J 2/00; B01J 6/008; B02C 23/00; B03C 1/00; B09B 5/00; B22F 2009/001; B22F 3/10; B22F 9/00; B28B 17/02; B28B 5/00; B29B 17/00; C01B 13/02; C01B 17/02; C01B 17/027; C01B 17/48; C01B 17/74; C01B 2203/0205;
(Continued)

(56) References Cited

U.S. PATENT DOCUMENTS

2012/0211366 A1    8/2012    Lee et al.

FOREIGN PATENT DOCUMENTS

CA    25889956 A1    5/2014

*Primary Examiner* — Deborah K Ware
(74) *Attorney, Agent, or Firm* — Verrill Dana, LLP

(57) ABSTRACT

The present invention is directed to a self-sufficient process for the production of biomass hydrolysate with reduced salt content as well as the de-salted hydrolysate produced after the inventive process and the use of the de-salted hydrolysate as a fermentation medium.

10 Claims, 1 Drawing Sheet

(51) Int. Cl.
  *C12P 19/02* (2006.01)
  *C13K 1/02* (2006.01)
  *D21C 1/02* (2006.01)
  *D21C 1/04* (2006.01)

(52) U.S. Cl.
  CPC .............. *D21C 1/02* (2013.01); *D21C 1/04* (2013.01); *C12P 2201/00* (2013.01); *C12P 2203/00* (2013.01)

(58) Field of Classification Search
  CPC ...... C01B 2203/0283; C01B 2203/043; C01B 2203/0445; C01B 2203/0475; C01B 32/05; C01B 32/20; C01B 32/50; C01B 32/60; C01B 33/187; C01B 3/32; C01G 21/02; C02F 1/001; C02F 1/66; C02F 1/683; C10G 11/18; C10G 1/00; C10G 1/02; C10G 1/10; C10G 31/08; C10G 33/00; C10G 45/00; C10G 57/00; C10G 75/04; C10G 7/00; C10G 7/003; C10G 7/06; C10J 2300/093; C10J 2300/0946; C10J 3/72; C10L 2290/544; C10L 9/10; C12M 47/06; C22B 13/00; C22B 15/00; C22B 21/00; C22B 7/00; C22B 9/00; E01C 5/04; E01C 5/06; E01C 5/065; F27B 17/00; H01M 10/54; H01M 8/00; H02K 55/02; H02K 7/09; Y10T 428/31996
  See application file for complete search history.

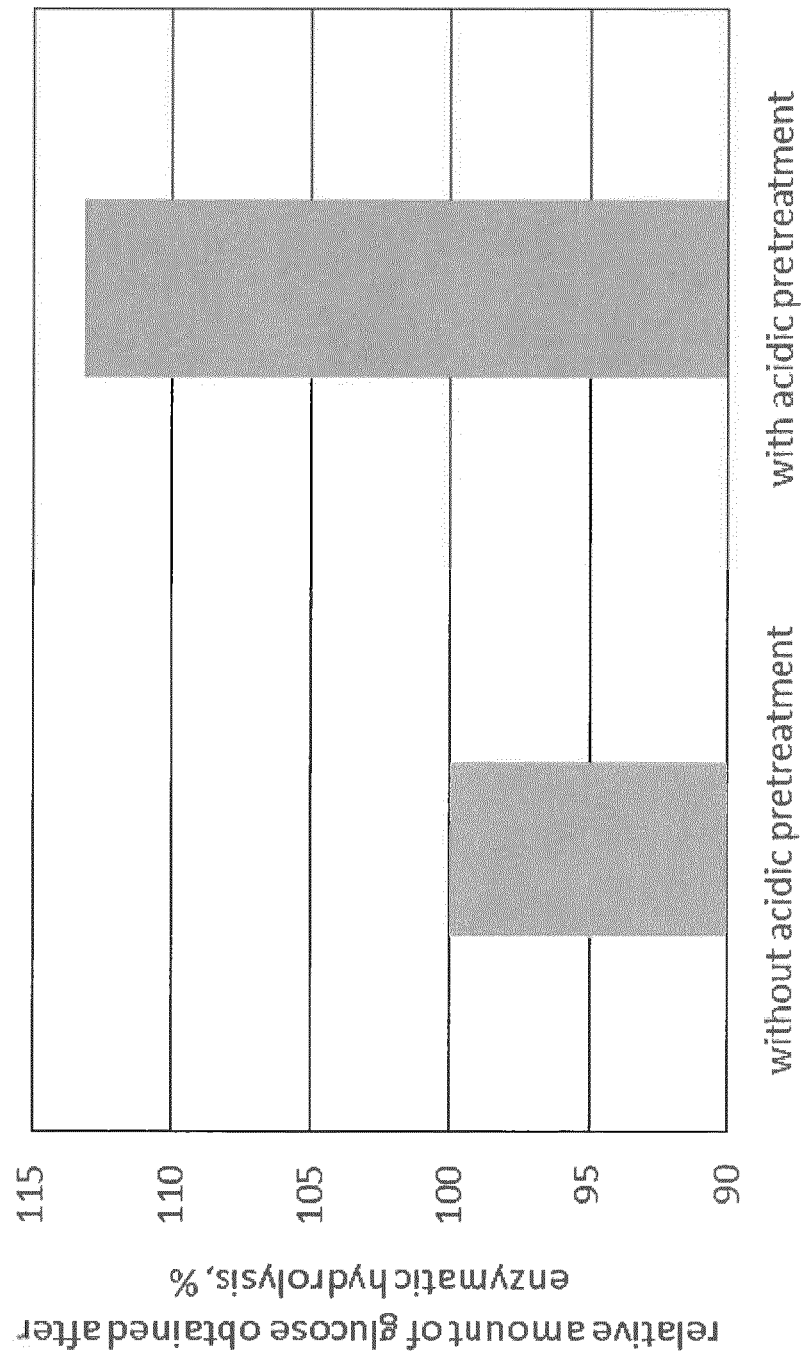

SELF-SUFFICIENT PROCESS FOR THE PRODUCTION OF BIOMASS HYDROLYSATE WITH REDUCED SALT CONTENT

The present invention is directed to a self-sufficient process for the production of biomass hydrolysate with reduced salt content as well as the hydrolysate produced after the inventive process and the use of the hydrolysate as a fermentation medium.

Biomass originating from agricultural residues such as sugar cane bagasse, wheat straw, barley straw and other saccharide- or polysaccharide- and protein-containing material are valuable sources not only for refined saccharides such as monomeric or dimeric sugars, but also for other components such as amino acids, proteins and minerals.

There are various processes known within the state of the art for separating components such as particularly sugars from sugar beets and sugar cane or grain. Solutions resulting from these so-called "first generation" substrates are almost pure sugar solutions and can be used in standard e.g. fermentation processes without further treatment and with no major impact on process efficiency. A drawback regarding the use of these substances is, however, that sugar beets, sugar cane and grains are valuable food products and their use within processes such as the production of biofuels and commodity chemicals is highly controversial.

In contrast thereto, solutions resulting from the hydrolysis of "second generation" substrates based on agricultural residues such as sugar cane bagasse, wheat straw or barley straw are complex mixtures of proteins, minerals and polymeric sugars. They also contain organic acids, colored particles, degradation products from lignin and other impurities. This makes these second generation hydrolysates unsuitable for further processing such as for example the preparation of poly lactic acid from lactic acid due to inhibition of fermentation and undesired coloring. Existing processes involving this type of hydrolysate also suffer from severe fouling in tubes, pipes and on membranes leading to frequent cleaning and replacement of process units.

Furthermore, these second generation substrates typically contain large amounts of lignin and the polymeric sugars are highly polymerized which make these substrates recalcitrant and difficult to convert. Therefore, these substrates require a pretreatment step in order to make them accessible for enzymatic hydrolysis. Within the state of the art anorganic acids like sulphuric acid are usually used which increases the costs of the process dramatically since not only the acid needs to be purchased, but also the waste-water treatment becomes more expensive.

Regarding industrial scale hydrolysate production, a key barrier is however not only the production of a high quality end product but also the expenditure for costs. Thus an efficient process with low energy and material consumption and low impact on the environment as well as a high biomass conversion capacity is of major importance.

It was therefore an object of the present invention to provide a process which meets these key criteria.

It has now been surprisingly found by the inventors of the present invention that this object can be met by a process comprising the steps
a) Providing a biomass;
b) Acidic pretreatment of the biomass;
c) Hydrolysis of the biomass to obtain a biomass hydrolysate;
d) Solid-liquid separation of the biomass hydrolysate to obtain a solid phase and a liquid phase;
e) Deionization of the liquid phase by electrodialysis using at least one bipolar membrane;
f) Separation of an acid and/or an alkaline fraction from the deionized liquid phase;
g) Addition of at least part of the separated acid fraction to step b)
wherein steps a) to g) are repeated at least once.

This process will not only provide a de-salted high quality hydrolysate suitable for refined applications but also guarantee an effective decomposition of the biomass with low material investments leading to an economically highly feasible process.

The term "biomass" as used within the present invention refers to any type of biomass known to a person skilled in the art as suitable for the inventive process. Particularly preferred is biomass of plant-origin. Within a further preferred embodiment, the initial dry matter content of the biomass is selected from 10 to 100 wt.-%, more preferred from 35 to 95 wt.-% and particularly preferred from 40 to 80 wt.-%. The term "dry matter" (d.m.) refers to the mass to biomass ratio determined after water and other volatile compounds have been removed from fresh tissue using an IR-balance. It is thereby particularly preferred to select a biomass whereby its dry matter contains at least 25 wt.-% of saccharides such as monomeric sugars, dimeric sugars and oligosaccharides and/or polysaccharides, more preferred at least 40 wt.-%, particularly preferred at least 60 wt.-%, further preferred at least 80 wt.-% of saccharides such as monomeric sugars, dimeric sugars and oligosaccharides and/or polysaccharides. Further, any mixtures of suitable biomasses are to be included within the term "biomass".

Particularly preferred biomass is "lignocellulose biomass".

The term "lignocellulose biomass" refers to residue-, waste- and/or by-products from forestry and agriculture, the food-processing and paper industry and communal waste. In particular, the term "lignocellulose biomass" as used within the present invention includes grain straw and/or spelt (such as wheat, rye, barley, oats), maize straw, stover and/or spindles, grasses such as *Sericea lespedeza*, switchgrass (*Panicum virgatum*), Napier grass (*Miscanthus*; China reed), Sudan grass (*Sorghum sudananse, Sorghum drummondi*), *Arundo donax*, barks, wood, wood residues, wood chips and/or wood chippings, fruit pulp, rice straw, banana leaves, empty fruit bunches and agave residues.

Further biomass suitable for the process are manure from stables, herbaceous materials, coffee grinds and waste from oil mills such as rapeseed pressed cake and sewage from mills, paper-making stock and waste water from paper mills, waste paper, vegetable and fruit leftovers.

Within a preferred embodiment of the process of the present invention, the biomass is selected from cellulose, hemicellulose and/or lignin-containing biomass.

Within a particularly preferred embodiment of the process of the present invention the biomass is selected from sugar beet pulp, sugar cane bagasse, sugar cane straw, wheat straw, wood and mixtures thereof.

Within another particularly preferred embodiment of the process of the present invention the biomass is lignocellulosic biomass from agricultural residues such as wheat straw, barley straw, soy bean straw, sugar cane bagasse, sugar cane leaves and stalks, sugar cane straw, maize straw, barley straw, stover and mixtures thereof.

The term "acidic pretreatment" as used within the present invention is to be understood as constituting any kind of treatment known to a person skilled in the art involving the use of an acid or combination of acids. It is within the scope of the present invention to add any kind of acid such as sulfuric acid, acetic acid, formic acid, lactic acid, phosphoric acid, nitric acid, citric acid, tartaric acid, succinic acid, hydrogen chloride or mixtures thereof, it is however preferred to only add acids generated during the deionization according to step e) of the inventive process. It is a particular advantage of the process of the present invention that no external acid(s) have to be added to the process, the process is self-sufficient regarding the use of acids. In case of a continuous process—repetition of process steps a) to g) at least once—no external acid has to be added to the first pretreatment step b) as organic acids already present within the biomass are sufficient to start the process. Therefore, the term "acidic pretreatment" as used within the present invention also comprises a treatment using the acid(s) already present within the biomass.

The acidic pretreatment is preferably carried out in combination with a mechanical treatment. It is also possible that the biomass provided within step a) of the inventive process has already undergone a mechanical treatment.

The term "mechanical treatment" refers to any mechanical treatment which leads to a comminution of the biomass. Mechanical comminution is preferably selected from the group consisting of mechanical processing, grinding, chopping, crushing, cutting, irradiation, milling such as dry milling, wet milling and vibratory ball milling, and combinations thereof.

A particularly preferred mechanical treatment according to the present invention is steam explosion. "Steam explosion" according to the present invention preferably comprises a pressurised hydrothermal treatment at a temperature of from 60 to 350° C., preferably from 80 to 300° C., particularly preferred from 100 to 250° C. and most preferred from 110 to 220° C. of the biomass material. In a preferred embodiment of the present invention the pressure is preferably selected from 1 to 100 bar, preferably from 2 to 50 bar, also preferred from 3 to 25 bar and most preferred from 5 to 15 bar. Reaction times during steam explosion have to be selected from 10 s to 2 h, preferably from 1 minute to 1.5 hours, and most preferred from 5 minutes to 1 hour to provide for efficient transformation of the biomass components in preparation for the following hydrolysis step. In a preferred embodiment, acid is added to the steam explosion process. The amount of acid added is preferably within the range of from 0.07 to 6.5 mol $H^+$ ions, more preferred 0.13 to 3.3 mol $H^+$ ions, most preferred 0.33 to 1.3 mol $H^+$ ions per kg dry matter of the biomass.

The term "hydrolysis of the biomass" as used within the present invention is to be understood as comprising any kind of hydrolysis known to a person skilled in the art as suitable for the inventive process. According to a particularly preferred embodiment of the present invention, hydrolysis of the biomass is carried out by enzymatic hydrolysis.

According to a preferred embodiment of the process of the present invention, enzymatic hydrolysis is carried out by contacting the pretreated biomass with an enzyme-composition containing at least one enzyme selected from the class of hydrolases.

The term "contacting" (or "contacted") comprises any kind of contacting of biomass with an enzyme composition known to a person skilled in the art as suitable for the inventive process. Within a preferred embodiment, the "contacting" of the biomass with the enzyme composition is carried out by adding the enzyme composition to the biomass. Further, it is particularly preferred that the addition of the enzyme composition is followed by or carried out concurrently with a mixing of the enzyme composition and the biomass.

The term "enzyme composition" refers to any composition comprising at least one enzyme selected from the class of hydrolases. The at least one enzyme selected from the class of hydrolases amounts preferably to from 1 to 99.99 wt.-% (relative to the weight of the enzyme composition), further preferred to from 5 to 99 wt.-%, particularly preferred to from 10 to 95 wt.-% and most preferred to from 20 to 90 wt.-% and may further contain at least one enzyme selected from the class of lyases. Within embodiments, wherein the enzyme-composition contains at least one enzyme selected from the class of lyases, the at least one enzyme selected from the class of hydrolases preferably amounts to from 0.01 to 50 wt.-% (relative to the weight of the enzyme composition), preferred to from 0.05 to 20 wt.-%, more preferred to from 0.08 to 5 wt.-% and most preferred to from 0.1 to 1 wt.-%.

Within a preferred embodiment, the enzyme composition contains cellulases, hemicellulases and/or pectinases.

Within a particularly preferred embodiment the enzyme composition contains at least one cellobiohydrolase (EC 3.2.1.-) and at least one endo-,4-β-glucanase (EC 3.2.1.4).

Within a particularly preferred embodiment, the enzyme composition contains at least one cellobiohydrolase (EC 3.2.1.-), at least one endo-,4-β-glucanase (EC 3.2.1.4), at least one β-glucosidase (EC 3.2.1.4), at least one glycoside hydrolase 61 (GH61 and CBM33), at least one endo-xylanases (EC 3.2.1.8) and at least one β-xylosidases (EC 3.2.1.37).

Within a particularly preferred embodiment the above defined enzyme composition further contains one or more enzymes selected from β-glucanase (EC 3.2.1.-), acetylxylan esterase (EC 3.1.1.72), acetylgalactan esterase (3.1.1.6)), α-arabinopyranosidase (3.2.1.-), α-galactosidase (EC 3.2.1.22), β-galactosidase (EC 3.2.1.23), α-glucuronidases (EC 3.2.1.139), β-mannase (EC 3.2.1.78), pectin methyl esterase (EC 3.1.1.11), pectin acetyl esterase (EC 3.1.1.-), rhamnogalacturonase (EC 3.2.1.-; GH28), rhamnogalacturonan acetylesterase (EC 3.1.1.86), rhamnogalacturonan endolyase (EC 4.2.2.23), rhamnogalacturonan lyase (EC 4.2.2.-) and β-mannosidases (EC 3.2.1.25), polygalacturonases (EC 3.2.1.15, 67, 82; GH28) and pectin/pectate lyases (EC 4.2.2.2, 6, 9, 10).

The terms "cellulases", "hemicellulases" and "pectinases" refer to any blend of enzymes which is involved in the hydrolytic degradation (depolymerization) of polymeric cellulose, hemicellulose and/or pectin to monomeric sugars. As used herein, the terms "cellulases", "hemicellulases" and "pectinases" refer to both naturally occurring and non-naturally occurring blends that include a plurality of enzymes as produced by an organism, for example a filamentous fungus. "Cellulases", "hemicellulases" and "pectinases" are preferably derived from fungi such as members of the subdivision Eumycota and Oomycota, including but are not limited to the following genera: *Aspergillus, Acremonium, Aureobasidium, Beauveria, Cephalosporium, Ceriporiopsis, Chaetomium, Chrysosporium, Claviceps, Cochiobolus, Cryptococcus, Cyathus, Endothia, Endothia mucor, Fusarium, Gllocladium, Humicola, Magnaporthe, Myceliophthora, Myrothecium, Mucor, Neurospora, Phanerochaete, Podospora, Paecilomyces, Pyricularia, Rhizomucor, Rhizopus, Schizophylum, Stagonospora, Talaromyces, Trichoderma, Thermomyces, Thermoascus, Thielavia, Toly-*

*pocladium*, *Trichophyton*, and *Trametes*. In a preferred implementation, the filamentous fungus is a *Trichoderma* species.

Within a preferred embodiment of the enzyme-composition the cellulases and/or pectinases are from a fungal source. Within a particularly preferred embodiment of the enzyme-composition, this fungal source is *Trichoderma reesei*.

The term "blend of enzymes" preferably refers to a blend of enzymes secreted from one single or more microbial sources. In some embodiments, enzymes for use in these blend(s) of enzymes can be prepared from one or more naturally occurring or engineered strains of filamentous fungi. Preferred strains are listed above. The desired ratio of enzyme components within the final blend(s) can be achieved by altering the relative amount of enzyme in the final blend e.g. by supplementation of purified or partially purified enzyme(s). In some embodiments, the final blend(s) may be supplemented with one or more enzyme activities that are not expressed endogenously, or expressed at relatively low level by the filamentous fungi, to improve the degradation of the cellulosic substrate to fermentable sugars. The supplemental enzyme(s) can be added as a supplement to the final blend(s) and the enzymes may be a component of a separate whole fermentation broth, or may be purified, or minimally recovered and/or purified.

The term "cellulase" refers to any enzyme capable of hydrolyzing cellulose polymers to shorter oligomers and/or glucose. Cellulases preferred within the enzyme composition include cellobiohydrolases (CBH) (EC 3.2.1.-), endo-1,4-β-glucanases (EG) (EC 3.2.1.4).), β-glucosidase (EC 3.2.1.4), cellobiose hydrolase (EC 3.2.1.21), glycoside hydrolase 61 (GH61 and CBM33), expansin, swollenin, loosinin and CIP Proteins (EC 3.1.1.-; CE15).

The term "hemicellulase" refers to any enzyme capable of degrading or supporting the degradation of hemicellulose. Hemicellulases preferred within the enzyme composition include β-glucanases (EC 3.2.1.-), endo-xylanases (EC 3.2.1.8), β-xylosidases (EC 3.2.1.37), acetylxylan esterase (EC 3.1.1.72), acetylgalactan esterase (3.1.1.6), acetyl mannan esterase, feruloyl esterase (EC 3.1.1.73), glucuronoyl esterase (EC 3.1.1.-), α-L-arabinofuranosidase (EC 3.2.1.55), α-arabinopyranosidase (3.2.1.-), α-galactosidase (EC 3.2.1.22), β-galactosidase (EC 3.2.1.23), α-glucuronidases (EC 3.2.1.139), β-mannase (EC 3.2.1.78), β-mannosidases (EC 3.2.1.25), mannan 1,4-mannobiosidase (EC 3.2.1.100), arabinogalactan endo-beta-1,4-galactanase (EC 3.2.1.89), endo-beta-1,3-galactanase (EC 3.2.1.90), galactan endo-beta-1,3-galactanase (EC 3.2.1.181, glucuronoarabinoxylan endo-1,4-beta-xylanase (EC 3.2.1.136), alpha-L-fucosidase (EC 3.2.1.51), coniferin beta-glucosidase (EC 3.2.1.126), xyloglucan hydrolases (EC 3.2.1.150, 151, 155), xylan α-1,2-glucuronosidase (EC 3.2.1.131), endo-xylogalacturonan hydrolase (EC 3.2.1.-; GH28), α-amylase (EC 3.2.1.1), glucan 1,4-α-glucosidase (EC 3.2.1.3), galactan 1,3-galactosidase (GH43), -1,4,-endogalactanase (EC 3.5.1.89; GH53), α-rhamnosidase (EC 3.2.1.40), β-rhamnosidase (EC 3.2.1.43), lignin peroxidase (EC 1.11.1.14), Mn peroxidase (EC 1.11.1.13), aryl-alcohol oxidase (EC 1.1.3.7), glyoxal oxidase (EC 1.1.3.), carbohydrate oxidases (EC 1.1.3.4, 9, 10), laccase (EC 1.10.3.2) and cellobiose dehydrogenase (EC 1.1.99.18).

The term "pectinase" refers to any enzyme capable of degrading or supporting the degradation of pectin. Pectinases preferred within the enzyme composition include polygalacturonases (EC 3.2.1.15, 67, 82; GH28), pectin/pectate lyases (EC 4.2.2.2, 6, 9, 10), pectin methyl esterase (EC 3.1.1.11), pectin acetyl esterase (EC 3.1.1.-), rhamnogalacturonase (EC 3.2.1.-; GH28), rhamnogalacturonan acetylesterase (EC 3.1.1.86), rhamnogalacturonan endolyase (EC 4.2.2.23), rhamnogalacturonan lyase (EC 4.2.2.-), rhamnogalacturonan galacturonohydrolase (EC 3.2.1.-), xylogalacturonan hydrolase (EC 3.2.1.-), pectin methylesterase (EC 3.1.1.11), beta-arabinofuranosidase (EC 3.2.1.55), beta-1,4-galactanase (EC 3.2.1.89), beta-1,3-galactanase (EC 3.2.1.90), beta-galactosidase (EC 3.2.1.23), alpha-galactosidase (EC 3.2.1.22), feruloyl acetyl esterase (EC 3.1.1.-), alpha-fucosidase (EC 3.2.1.51), (beta-fucosidase) (EC 3.2.1.38), beta-apiosidase (EC 3.2.1.-), alpha-rhamnosidase (EC 3.2.1.40), beta-rhamnosidase (EC 3.2.1.43), alpha-arabinopyranosidase (EC beta-glucuronidase (EC 3.2.1.31), alpha-glucuronidase (EC 3.2.1.139), beta-xylosidase (EC 3.2.1.37) and alpha-xylosidase (EC 3.2.1.x).

The enzymes are classified according nomenclatures that are either based on the International Union of Biochemistry and Molecular Biology's Enzyme Nomenclature and Classification (http://www.chem.qmul.ac.uk/iubmb/enzyme/) or on Carbohydrate-Active EnZYmes (http://www.cazy.org/) database.

The term "activity" of an enzyme refers to the catalytic activity of the enzyme under appropriate conditions under which the enzyme serves as a protein catalyst, which converts specific polymeric or artificial substrates to specific oligomeric or monomeric products. In this context the term "appropriate conditions" is well known to and applicable by a person skilled in the art.

In a preferred embodiment the hydrolysis of biomass is carried out for a time sufficient to hydrolyze at least 20 wt.-%, preferably at least 30 wt.-%, more preferred at least 50 wt.-% and most preferred at least 60 wt.-% of the biomass. Within a further preferred embodiment the hydrolysis of the biomass is carried out for a time sufficient to hydrolyze from 10 to 100 wt.-%, preferably from 20 to 90 wt.-% even more preferred from 30 to 85.0 wt.-% and most preferred from 40 to 75 wt.-% of the cellulose of the biomass. The term "hydrolyze" is to be understood as the hydrolytic conversion of insoluble polymeric components of the biomass to soluble monomeric, dimeric and/or oligomeric compounds by chemical, physical and/or enzymatic processes such as hydrolysis.

Within a particularly preferred embodiment the hydrolysis of biomass is carried out for 1 minute to 136 hours, more preferred for 30 minutes to 112 hours, particularly preferred for 1 hour to 100 hours, even more preferred for 4 hours to 96 hours also particularly preferred from 12 hours to 85 hours.

Within a further preferred embodiment the hydrolysis of biomass is carried out until the content of remaining insoluble solids is less than 40 wt.-%, preferably less than 30 wt.-%, even more preferred less than 20 wt.-% and most preferred less than 15 wt.-%. In a further preferred embodiment the hydrolysis of biomass is carried out until the content of remaining insoluble solids is from 5 to 40 wt.-%, preferably from 8 to 30 wt.-% and most preferred from 10 to 25 wt.-%.

Within another preferred embodiment the hydrolysis of biomass is carried out until the biomass is liquefied to at least 50%, preferably at least 60% and most preferred at least 80%, wherein a liquefaction of from 60 to 90% is particularly preferred.

The reaction temperature during hydrolysis is preferably selected from 25 to 80° C., more preferred selected from 30 to 75° C. and particularly preferred from 35 to 65° C. In another preferred embodiment the hydrolysis of biomass is carried out for 1 to 120 hours, preferably 2 to 110 hours, more preferred 3 to 100 hours, wherein the temperature is selected from 35 to 75° C. or from 45 to 65° C.

Within another preferred embodiment, the pH during hydrolysis is preferably selected from 4 to 6.5, particularly preferred from 4.5 to 5.5.

Optimum dosage levels will vary considerably depending upon the substrate and the pretreatment technologies used. The enzyme composition is preferably added to the biomass in an amount of from 0.01 to 24 wt.-% of the dry matter of the biomass, more preferred 0.025 to 12 wt.-% of the dry matter of the biomass, particularly preferred being 0.05 to 6 wt.-% of the dry matter of the biomass and most preferred from 0.1 to 3 wt.-% of the dry matter of the biomass. The total enzyme (protein) concentration was determined by the Bradford method with bovine serum albumin as a reference standard (Bradford, M., 1976).

The hydrolysis of biomass is carried out within any kind of vessel known to a person skilled in the art as suitable for the inventive process, preferably within a reactor. Suitable reactors are within the knowledge of a person skilled in the art. Preferable vessels/reactors include but are not limited to vessels/reactors comprising a stirring measure and/or a measure for pumping over or recirculating the biomass content within the reactor. Further preferred measures of preferred reactors include but are not limited to measures for temperature and/or pH-controlling and regulation of temperature and/or pH.

The term "biomass hydrolysate" as used within the present invention is to be understood as a depolymerized biopolymer which was depolymerized by a hydrolysis reaction. Hydrolysis reaction is to be understood as the cleavage of chemical bonds by the addition of water. One way to perform hydrolysis technically is to add hydrolase enzymes to the biomass.

Within a preferred embodiment, the biomass hydrolysate comprises at least 50 wt.-% saccharides in the form of monomeric and dimeric sugars, preferably at least 65 Wt.-%, more preferred at least 75 wt.-%, also preferred at least 85 wt.-% and most preferred 99 wt.-% all relative to the dry matter (d.m.) of the biomass. Within a further preferred embodiment, the biomass hydrolysate comprises amino acids, oligopeptides, minerals, oligosaccharides and/or proteins as well as organic acids. The content in minerals is preferably at least 0.5 wt.-% salts, preferably at least 1 wt.-%, more preferred at least 2 wt.-% and most preferred 3 wt.-% all relative to the dry matter (d.m.) of the biomass. The biomass hydrolysate may comprise organic acids such as formic acid, acetic acid, galacturonic acid and lactic acid. It may also comprise the following degradation products: phenolic compounds such as 4-hydroxy-3-methoxyphenyl and 4-hydroxy-3,5-dimethoxyphenyl, ferulic acid, 4-hydroxybenzoic acid, levulinic acid, furfurals, 5-hydroxymethylfurfural, tannins and terpenes.

According to step (d) of the inventive process a solid and a liquid phase are separated from the biomass hydrolysate. The separation of the solid and the liquid phase of the biomass hydrolysate (in the following "liquid phase" or "solid phase") may be carried out by any measure known to a person skilled in the art as suitable for the inventive purpose and is preferably carried out by filtration, centrifugation, decantation or pressing e.g. by a screw-press. Preferred is a filter press, most preferred a membrane filter press. In a preferred embodiment, the filter cloth of the filter press has a cloth air permeability of from 2 to 10 L/dm$^2$/min. Filtration aids such as diatomaceous earth or kieselguhr or perlite can also be added during the filtration, preferably in concentrations of from 0.1 wt.-% to 10 wt.-%, more preferably between 0.5 wt.-% to 5 wt.-%, and most preferred between 1 wt.-% and 3 wt.-%.

After the separation of the solid and the liquid phase, deionization of the liquid phase according to step (e) is carried out by electrodialysis using at least one bipolar membrane. Within the present invention "electrodialysis using at least one bipolar membrane" is to be understood as any technique comprising the use of three different types of membranes suitable to remove salts by removing ions such as e.g. $Na^+$, $K^+$, $Mg^{2+}$, $Ca^{2+}$, $SO4^{2-}$, $PO3^{3-}$, $Cl^-$ and split $H_2O$ present in the liquid phase. Electrodialysis using at least one bipolar membrane preferably comprises the use of a cation exchange membrane, an anion exchange membrane and a catalytic intermediate layer, a so-called "bipolar membrane", to enable the splitting of the water within the liquid phase into protons and hydroxide ions. Through the combination of the selective removal of salts by the cation and anion exchange membranes with the simultaneous water dissociation on the catalytic intermediate layer, the respective inorganic or organic acid and base fractions are formed.

When using electrodialysis using at least one bipolar membrane for the deionization, the ions removed from the solution are preferably recovered in a liquid called "concentrate". In this respect it is particularly preferred to add a liquid into a compartment of the electrodialysis unit before the start of the deionizaiton. In a further preferred embodiment, this liquid is not replaced after stopping the deionization of a given volume, but the concentrate is reused in repeated deionizations over at least 2 cycles, more preferred at least 4 cycles, particularly preferred 6 cycles and most preferred 10 cycles.

Within a preferred embodiment, at least one cation exchange membrane, at least one anion exchange membrane and at least one catalytic intermediate layer or bipolar membrane are used. Within a further preferred embodiment, at least two sets of these membranes are arranged in series, preferably at least 4 sets, further preferred at least 6 sets and most preferred at least 10 sets. Within a particularly preferred embodiment, all three membranes or all sets of membranes as defined before are arranged within a single device.

The deionization is preferably carried out at a temperature within the range of from 5° C. to 80° C., more preferred within the range of from 10° C. to 75° C., most preferred within the range of from 15° C. to 70° C. The pressure drop through the electrodialysis cell is preferably below 1 bar, more preferred below 0.5 bar. Within a further particularly preferred embodiment, deionization is carried out until the conductivity of the solution is reduced to at least 10 mS/cm, more preferred to at least 6 mS/cm particularly preferred to at least 4 mS/cm and most preferred to at least 2 mS/cm.

In a further preferred embodiment, the deionization by electrodialysis using at least one bipolar membrane is followed by capacitive deionization. The capacitive deionization is preferably applied as so-called "membrane capacitive deionization", i.e. by inserting a cation exchange membrane and an anion exchange membrane into the capacitive deionization unit. If the electrodialysis using at least one bipolar membrane is followed by membrane capacitive deionization, the electrodialysis is preferably performed until the conductivity of the solution is reduced to at least 10 mS/cm, more preferred to at least 6 mS/cm particularly preferred to at least 4 mS/cm and most preferred to at least 2 mS/cm before switching to membrane capacitive deionization. The membrane capacitive deionization following the electrodialysis is then used to further decrease the conductivity of the solution preferably to at least 8 mS/cm, more preferred to at least 6 mS/cm, particularly preferred to at least 4 mS/cm and most preferred to at least 2 mS/cm.

In a another preferred embodiment, the deionization by electrodialysis using at least one bipolar membrane is followed by ion exchange chromatography. If the electrodialysis using at least one bipolar membrane is followed by ion exchange chromatography, the electrodialysis is preferably performed until the conductivity of the solution is reduced to at least 10 mS/cm, more preferred to at least 6 mS/cm particularly preferred to at least 4 mS/cm and most preferred to at least 2 mS/cm before switching to membrane capacitive deionization. The ion exchange chromatography following the electrodialysis is then used to further decrease the conductivity of the solution preferably to at least 8 mS/cm, more preferred to at least 6 mS/cm, particularly preferred to at least 4 mS/cm and most preferred to at least 2 mS/cm.

Within the present invention, "ion exchange" is defined as an exchange of ions between a solution containing at least one ion and a solid polymeric or mineralic ion exchange material, wherein an ion dissolved in the solution is exchanged and replaced through contact with the ion exchange material by an ion of the same charge.

According to step f) of the inventive process the acid and alkaline fraction are separated from the deionized liquid phase. The deionization step e) therefore generates an acid fraction, an alkaline fraction and a de-salted liquid phase. Separation according to the present invention can be carried out by any method or means known to a person skilled in the art as suitable for the inventive process and is preferably carried out in a continuous manner during the deionization step.

Depending on the salt content of the liquid phase, the acid fraction may contain one or more acids such as e.g. HCl, formic acid, acetic acid, lactic acid, sulfuric acid, phosphoric acid, nitric acid, citric acid and succinic acid. The alkaline fraction may contain one or more alkalines such as e.g. NaOH, KOH, $Mg(OH)_2$ and $Ca(OH)_2$. Within a preferred embodiment, the alkaline fraction has a pH of from 9 to 14, more preferred from 12 to 13. Within another preferred embodiment, the acid fraction has a pH of from 1 to 5, more preferred from 2 to 4.

According to step g) of the inventive process, at least part of the separated acid fraction is added to step b) of the process. It is thereby preferred to add from 5 to 99 wt.-% of the separated acid to step b) of the process, preferably from 10 to 98 wt.-%, further preferred from 15 to 97 wt.-% and most preferred from 30 to 96 wt.-%. Within a particularly preferred embodiment of the present invention, all of the separated acid fraction is added to step b) of the process.

By adding at least part of the acid fraction to step b) of the inventive process, the acidic pretreatment of the biomass can be carried out without the need to use and buy further raw material. This leads not only to a reduction of purchase and logistic costs but also to a reduction of disposal costs. Sulfuric acid, which is usually used within such processes due to its availability in high quantities at low purchasing costs, requires an extensive and costly waste management.

Within a further preferred embodiment of the process of the present invention, at least part of the separated alkaline fraction is added to step c) of the process. Within a particularly preferred embodiment the separated alkaline fraction is added to step c) until the biomass reaches a pH in the range of from 4.5 to 5.5, most preferred is a pH of 5. Utilization of the separated alkaline fraction within step c) of the inventive process leads to further cost reductions.

Another application of the separated alkaline fraction is the utilization for cleaning in place (cip) of one or more of the devices used within the process.

Within a preferred embodiment of the inventive process, the temperature of the biomass hydrolysate is adjusted before subjecting the biomass hydrolysate to the solid-liquid separation according to step d). The temperature is thereby preferably selected from the range of from 50 to 95° C., preferably of from 60 to 90° C., further preferred of from 65 to 85° C. The adjustment is to be carried out by any measure known to a person skilled in the art as suitable for the inventive process. Within a particularly preferred embodiment, at least one acid is added to the temperature-adjusted biomass hydrolysate. It is within the scope of the present invention to add at least one organic and/or at least one inorganic acid, whereas the at least one acid is preferably selected from the group consisting of acetic acid, formic acid, lactic acid, galacturonic acid, citric acid, sulfuric acid, phosphoric acid, hydrochloric acid, nitric acid and mixtures thereof. Within a further preferred embodiment of the present invention a part of the acid fraction separated according to step f) of the inventive process is added to the biomass hydrolysate. Within a preferred embodiment, the at least one acid is selected from acids with a pKa value below 5.0, preferably from acids with a pKa value below 3.5. Within a further preferred embodiment, the at least one acid is added to the biomass hydrolysate until a pH of from 1.5 to 4.5, preferably from 2.0 to 4.0 and most preferred of from 2.5 to 3.5 is reached.

Steps a) to g) as defined above are to be repeated at least once. It is thereby preferred to repeat steps a) to g) from 2 to 100000 times, preferably from 10 to 70000 times, more preferred from 15 to 50000 times and most preferred from 17 to 10000 times. Within a particularly preferred embodiment of the process of the present invention, the process is carried out as a continuous process. It is within the scope of the present invention that a cleaning step of a vessel and/or any other part of the system is carried out at any time in between or after steps a) to g). The cleaning may be carried out by any measure known to a person skilled in the art as suitable for the inventive purpose and may also include exchange of one or more parts of the system. Within a further preferred embodiment, steps a) to g) are at least partially carried out simultaneously.

Carrying out steps a) to g) of the inventive process will lead to a composition which is referred to as "de-salted hydrolysate" or "purified hydrolysate" within the scope of the present application.

Another aspect of the present invention pertains to a de-salted hydrolysate prepared according to the inventive process as defined herein. The salt content of the de-salted hydrolysate is preferably at most 80%, preferably at most 60%, more preferred at most 40%, more preferred at most 20%, and most preferred at most 10% all relative to the salt content after hydrolysis of the substrate.

The present invention further pertains to the use of the de-salted hydrolysate prepared according to the inventive process as a fermentation medium.

Valuable organic compounds resulting from bacterial fermentation of the de-salted hydrolysate comprise but are not limited to organic acids (such as acetic acid, lactic acid, succinic acid, itaconic acid, fumaric acid, propionic acid, and glucuronic acid), amino acids (such as glutamic acid, leucine, lysine, threonine, aspartic acid, phenylalanine, cysteine), caprolactams (such as alpha-amino-caprolactam), antibiotics (such as bleomycin, virginiamycin, lincomycin, monensin, blasticidin, tetracycline), vitamins (such as vitamin B2, B12 and C), enzymes, nucleotides/nucleosides (such as NADH, ATP, cAMP, FAD, coenzyme A), biogas, biopolymers (such as polyhydroxybutyrate, polyamides/fibroins), proteins, polysaccharides (such as xanthan, dextran), amino glucans (such as hyaluronic acid) as well as organic solvents and biofuels (such as acetone, ethanol, butanol, propanediol).

Valuable organic compounds resulting from yeast fermentation of the de-salted hydrolysate comprise but are not limited to organic solvents (e.g. ethanol, propanol), nucleotides (e.g. RNA), biosurfactants (e.g. sophorose lipids), enzymes and biopolymers (e.g. spidroins).

Valuable organic compounds resulting from fungal fermentation of the de-salted hydrolysate comprise organic acids (such as citric acid, fumaric acid, itaconic acid), antibiotics (such as penicillin, cephalosporin), enzymes, and polysaccharides (such as chitin).

In a further preferred embodiment of this process the organic compound is selected from alcohols, organic acids, biopolymers, antibiotics, amino acids, caprolactams, polysaccharides, organic solvents, biofuels, aminoglucans, nucleotides/nucleosides, vitamins, biosurfactants, enzymes and mixtures thereof.

In the following particularly preferred embodiments of the inventive process are described which are not to be understood as limiting the invention in any respect.

Particularly Preferred Embodiment 1

Particularly preferred is a process for the production of de-salted biomass hydrolysate comprising the steps
a) Providing a lignocellulosic biomass, preferably selected from cereal straw and bagasse;
b) Acidic pretreatment of the biomass;
c) Enzymatic hydrolysis of the biomass to obtain a biomass hydrolysate;
d) Solid-liquid separation of the biomass hydrolysate to obtain a solid phase and a liquid phase;
e) Deionization of the liquid phase by electrodialysis using at least one bipolar membrane;
f) Separation of an acid and/or an alkaline fraction from the deionized liquid phase;
g) Addition of at least part of the separated acid fraction to step b)
wherein steps a) to g) are repeated at least once.

Particularly Preferred Embodiment 2

Particularly preferred is a process for the production of de-salted biomass hydrolysate as defined within particularly preferred embodiment 1 wherein the pretreatment is carried out by steam explosion.

Particularly Preferred Embodiment 3

Particularly preferred is a process for the production of de-salted biomass hydrolysate as defined within particularly preferred embodiment 1 or 2 wherein the biomass hydrolysate is set to a pH from 4.5 to 5.5 preferably a pH of 5, and a temperature of from 50 to 95° C., preferably a temperature of 65 to 85° C.

Particularly Preferred Embodiment 4

Particularly preferred is a process for the production of de-salted biomass hydrolysate as defined within particularly preferred embodiment 1, 2 or 3 wherein the solid-liquid separation is carried out by a filter press, preferably a membrane filter press.

Particularly Preferred Embodiment 5

Particularly preferred is a process for the production of de-salted biomass hydrolysate as defined within any of particularly preferred embodiments 1 to 4, wherein electrodialysis is carried out using at least one cation exchange membrane, at least one anion exchange membrane and at least one bipolar membrane.

Particularly Preferred Embodiment 6

Particularly preferred is a process for the production of de-salted biomass hydrolysate as defined within particularly preferred embodiment 5, wherein electrodialysis is carried out by at least two sets of membranes each consisting of one cation exchange membrane, one anion exchange membrane and one bipolar membrane wherein at least 4 sets are more preferred and at least 6 sets are particularly preferred wherein at least 10 sets are most preferred.

Particularly Preferred Embodiment 7

Particularly preferred is a process for the production of de-salted biomass hydrolysate as defined within any of particularly preferred embodiments 1 to 6, wherein electrodialysis is followed by membrane capacitive deionization or ion exchange chromatography.

Particularly Preferred Embodiment 8

Particularly preferred is a process for the production of de-salted biomass hydrolysate as defined within any of particularly preferred embodiments 1 to 7, wherein steps a) to g) are repeated at least 50 times, preferably at least 100 times.

Particularly Preferred Embodiment 9

Particularly preferred is a process for the production of de-salted biomass hydrolysate as defined within any of particularly preferred embodiments 1 to 7, wherein the process is carried out in a continuous fashion.

Particularly Preferred Embodiment 10

Particularly preferred is a process for the production of de-salted biomass hydrolysate as defined within any of particularly preferred embodiments 1 to 9, wherein the pressure drop through the electrodialysis cell is preferably below 1 bar and/or wherein deionization is carried out until the conductivity of the liquid phase is reduced to at least 10 mS/cm.

EXAMPLE AND FIGURE

The present invention is now described by the following example and FIGURE. The example and FIGURE are for illustrative purposes only and is not to be understood as limiting the invention.

FIG. 1 shows the relative amount of glucose recovered during the enzymatic hydrolysis of the biomass when the biomass is pretreated without addition of acid (left column) and when the biomass is pretreated with addition of acid (inventive process) (right column) when carrying out the process of the present invention according to example 1.

Cereal straw with a dry matter content of 45 wt.-% was pretreated by steam explosion (220° C.). After the steam explosion, the so pretreated cereal straw ("substrate") was introduced into a stirred tank (Labfors, Infors AG, Switzerland). An enzyme composition containing 91.3 wt.-% Celluclast® (Cellulase from *Trichoderma reesei* ATCC 26921, C2730 Sigma) and 8.7 wt.-% Glucosidase (49291 Sigma) was added to the substrate at an enzyme to solid ratio of 0.5 wt.-% to hydrolyze the substrate to obtain a slurry. The hydrolysis was carried out at 50° C., pH 5.0 for 72 hours with stirring at 50 rpm. After hydrolysis, the slurry was heated to 70° C. for 1 h while stirring at 200 rpm and then the pH was set to 2.5 using 1 M $H_2SO_4$. The so-treated slurry was then filtered using a filter press with filter cloth having a cloth air permeability of 5 $L/dm^2/min$ at a constant pressure of 3 bar to obtain a liquid and a solid phase. The liquid phase was then deionized using electrodialysis with bipolar membranes (ED64004, PCCell) with a membrane stack composed of 10 bipolar membranes (PCCell), 10 anion exchange membranes (PC 200D, PCCell) and 9 cation exchange membranes (PC SK, PCCell). The electrodialysis was performed at 32° C. for a duration of 2 h and with pump rates of 50 L/h for the diluate and the concentrate. After 2 h, the conductivity decreased by 83% leading to a de-salted hydrolysate. Simultaneously, 7.1 g/l of an acid fraction with a pH of 2 was produced during the electrodialysis. This fraction can be used for the acid pretreatment of biomass, thus significantly reducing material costs and waste. It covers the amount of acid needed for the acidic pretreatment of the same amount of biomass as initially used by 160%.

The use of acid in the pretreatment of biomass is very advantageous, as it permits to recover 13% more glucose from the biomass during the enzymatic hydrolysis in comparison to the pretreatment without addition of acid. The results are shown in FIG. 1.

The invention claimed is:

1. Process for the production of de-salted biomass hydrolysate comprising the steps
   a) Providing a biomass;
   b) Acidic pretreatment of the biomass;
   c) Hydrolysis of the biomass to obtain a biomass hydrolysate;
   d) Solid-liquid separation of the biomass hydrolysate to obtain a solid phase and a liquid phase;
   e) Deionization of the liquid phase by electrodialysis using at least one bipolar membrane;
   f) Separation of an acid and/or an alkaline fraction from the deionized liquid phase;
   g) Addition of at least part of the separated acid fraction to step b)
   wherein steps a) to g) are repeated at least once.

2. Process according to claim 1, wherein the pretreatment is carried out by steam explosion.

3. Process according to claim 1, wherein all of the separated acid fraction is added to step b).

4. Process according to claim 1, wherein the hydrolysis of the biomass is carried out by enzymatic hydrolysis.

5. Process according to claim 4, wherein at least part of the separated alkaline fraction is added to step c).

6. Process according to claim 5, wherein the at least part of the separated alkaline fraction is added to step c) until the biomass has a pH in the range of from 4.5 to 5.5.

7. Process according to claim 1, wherein the temperature of the biomass hydrolysate is set to a temperature selected from the range of from 50 to 95° C.

8. Process according to claim 1, wherein at least part of the separated acid fraction is added to the biomass hydrolysate until the pH of the separated liquid phase is set to a pH selected from the range of from pH 1.5 to 4.5.

9. Process according to claim 1, wherein the biomass is lignocellulose biomass.

10. Process according to claim 1, wherein the electrodialysis using at least one bipolar membrane is followed by membrane capacitive deionization or ion exchange chromatography.

* * * * *